US012614339B2

(12) United States Patent
Chen et al.

(10) Patent No.: US 12,614,339 B2
(45) Date of Patent: Apr. 28, 2026

(54) THREE-DIMENSIONAL CT IMAGING METHOD AND APPARATUS

(71) Applicant: NORTH UNIVERSITY OF CHINA, Shanxi (CN)

(72) Inventors: Ping Chen, Shanxi (CN); Zhiqing Wei, Shanxi (CN); Sukai Wang, Shanxi (CN); Jiaotong Wei, Shanxi (CN); Xiaojie Zhao, Shanxi (CN); Yangxu Wu, Shanxi (CN)

(73) Assignee: NORTH UNIVERSITY OF CHINA, Shanxi (CN)

( * ) Notice: Subject to any disclaimer, the term of this patent is extended or adjusted under 35 U.S.C. 154(b) by 0 days.

(21) Appl. No.: 19/023,894

(22) Filed: Jan. 16, 2025

(65) Prior Publication Data

US 2025/0391100 A1     Dec. 25, 2025

(30) Foreign Application Priority Data

Jun. 25, 2024     (CN) .......................... 202410831945.1

(51) Int. Cl.
*G06T 15/08* (2011.01)
*G06T 3/40* (2006.01)
(Continued)

(52) U.S. Cl.
CPC ............... *G06T 15/08* (2013.01); *G06T 3/40* (2013.01); *G06V 10/44* (2022.01); *G16H 30/20* (2018.01); *G16H 30/40* (2018.01)

(58) Field of Classification Search
CPC .......... G06T 15/08; G06T 3/40; G16H 30/20; G16H 30/40; G06V 10/44
(Continued)

(56) References Cited

U.S. PATENT DOCUMENTS 12,016,717 B2     6/2024     Guo et al.
2020/0305806 A1     10/2020     Tang et al.
(Continued)

FOREIGN PATENT DOCUMENTS

CN     109745062 A     5/2019
CN     114004929 A     2/2022
(Continued)

OTHER PUBLICATIONS

Xueqin Sun et al., Reconstruction method suitable for fast CT imaging, Optics Express, published May 6, 2024, Taiyuan, CN (16 pages).
(Continued)

*Primary Examiner* — Jin Ge
(74) *Attorney, Agent, or Firm* — REISING ETHINGTON, P.C.

(57)     ABSTRACT

The disclosure provides a three-dimensional CT imaging method and apparatus. The method includes: collecting two DR images with a perpendicular relationship for an object to be imaged; inputting the two DR images into a preset three-dimensional volume reconstruction model to obtain a three-dimensional volume of the object outputted by the three-dimensional volume reconstruction model; and slicing the three-dimensional volume to obtain three-dimensional CT imaging of the object, wherein the preset three-dimensional volume reconstruction model is trained using multiple training samples, each training sample comprising: a DR image group composed of two DR images with a perpendicular relationship, a pseudo-sinogram corresponding to the DR image group, and a three-dimensional volume corresponding to the DR image group.

17 Claims, 8 Drawing Sheets

(51) Int. Cl.

| | | |
|---|---|---|
| *G06V 10/44* | (2022.01) | |
| *G16H 30/20* | (2018.01) | |
| *G16H 30/40* | (2018.01) | |

(58) Field of Classification Search
USPC ......................................................... 345/419
See application file for complete search history.

(56) References Cited

U.S. PATENT DOCUMENTS

| | | | |
|---|---|---|---|
| 2021/0074036 A1* | 3/2021 | Fuchs .................... | A61B 6/032 |
| 2021/0192810 A1* | 6/2021 | Paysan .................. | G06T 11/008 |
| 2022/0405990 A1* | 12/2022 | Chen ..................... | G06T 11/006 |
| 2023/0011759 A1* | 1/2023 | Lu ............................. | G06T 5/20 |
| 2023/0326596 A1 | 10/2023 | Lu et al. | |
| 2025/0157033 A1* | 5/2025 | Golden ................. | G16H 70/20 |

FOREIGN PATENT DOCUMENTS

| | | |
|---|---|---|
| CN | 119784931 A | 4/2025 |
| WO | WO2022127496 A1 | 6/2022 |

OTHER PUBLICATIONS

Niu Xiaowei, Research on CT image reconstruction and artifact correction algorithm, published Jan. 15, 2024 (61 pages).

Chinese Office Action for Chinese Application No. 202410831945.1 dated May 6, 2025 (32 pages).

Danil Kazimirov et al., Adaptive automated sinogram normalization for ring artifacts suppression in CT, Optics Express, May 2024, pp. 17606-17643, vol. 32, No. 10.

Qian Yufei, in-depth Learning Based Sparse Angle CT Reconstruction Study, Chinese Excellent Master's Theses Journal of Medical and Health Science and Technology, Feb. 15, 2021, E060-356, No. 02.

* cited by examiner

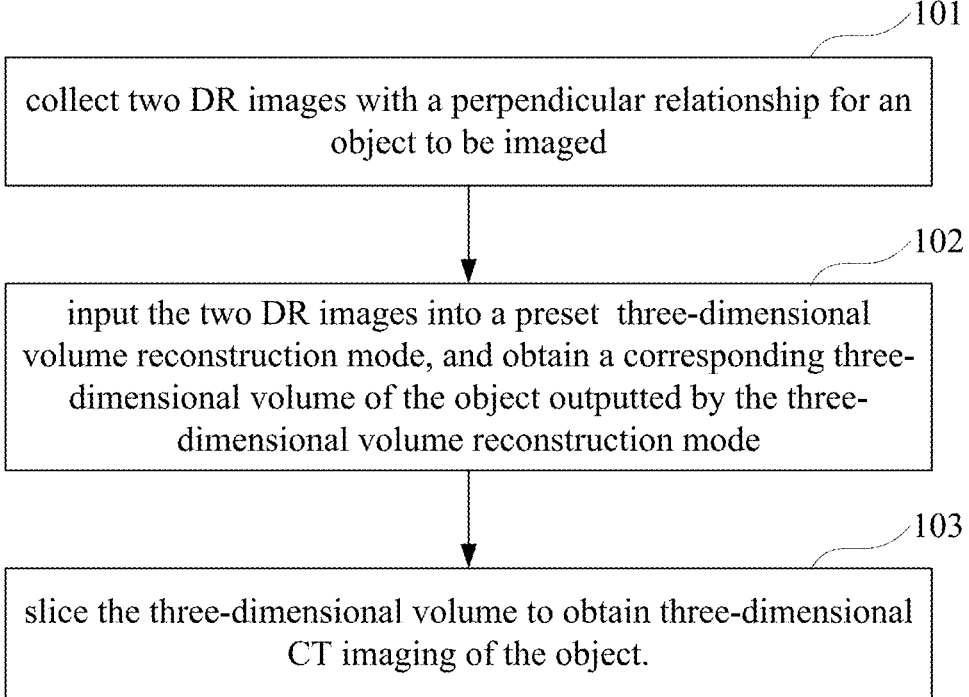

101 collect two DR images with a perpendicular relationship for an object to be imaged

102 input the two DR images into a preset three-dimensional volume reconstruction mode, and obtain a corresponding three-dimensional volume of the object outputted by the three-dimensional volume reconstruction mode

103 slice the three-dimensional volume to obtain three-dimensional CT imaging of the object.

Fig.1

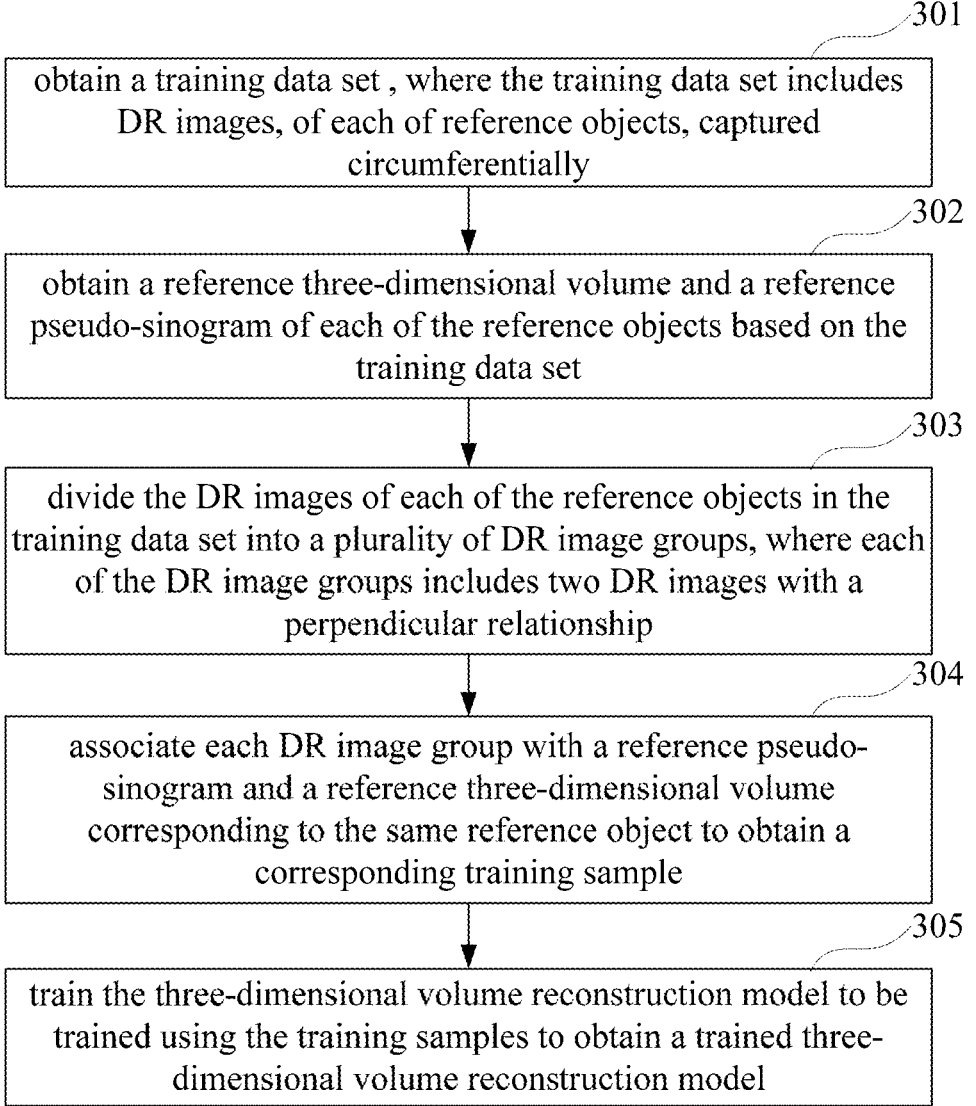

301 obtain a training data set , where the training data set includes DR images, of each of reference objects, captured circumferentially

302 obtain a reference three-dimensional volume and a reference pseudo-sinogram of each of the reference objects based on the training data set

303 divide the DR images of each of the reference objects in the training data set into a plurality of DR image groups, where each of the DR image groups includes two DR images with a perpendicular relationship

304 associate each DR image group with a reference pseudo-sinogram and a reference three-dimensional volume corresponding to the same reference object to obtain a corresponding training sample

305 train the three-dimensional volume reconstruction model to be trained using the training samples to obtain a trained three-dimensional volume reconstruction model

Fig.3A

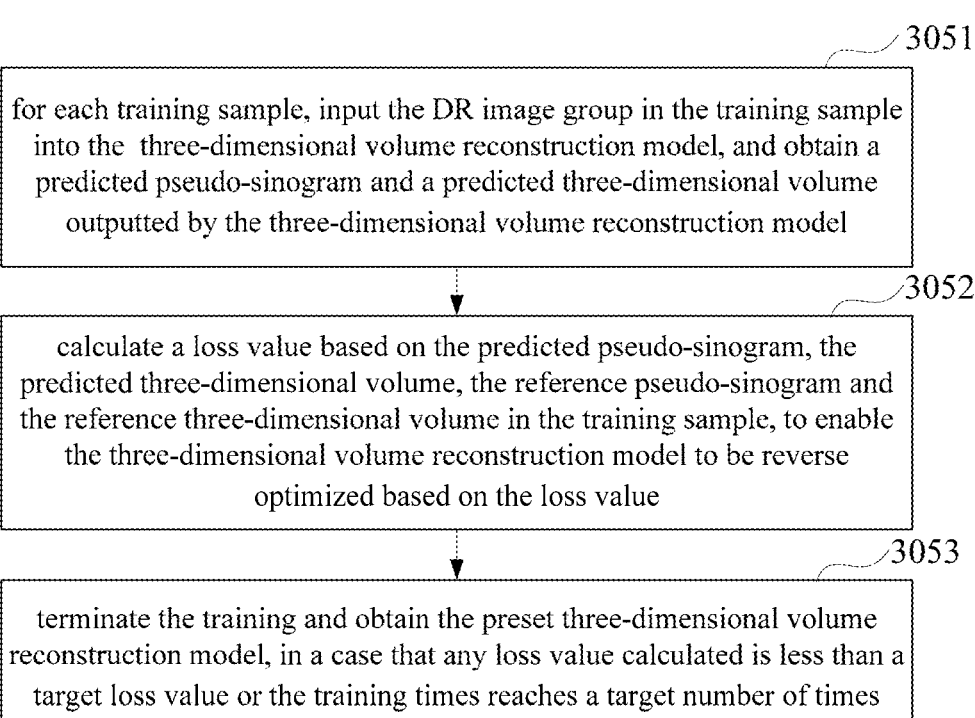

3051 for each training sample, input the DR image group in the training sample into the three-dimensional volume reconstruction model, and obtain a predicted pseudo-sinogram and a predicted three-dimensional volume outputted by the three-dimensional volume reconstruction model

3052 calculate a loss value based on the predicted pseudo-sinogram, the predicted three-dimensional volume, the reference pseudo-sinogram and the reference three-dimensional volume in the training sample, to enable the three-dimensional volume reconstruction model to be reverse optimized based on the loss value

3053 terminate the training and obtain the preset three-dimensional volume reconstruction model, in a case that any loss value calculated is less than a target loss value or the training times reaches a target number of times

Fig.3B

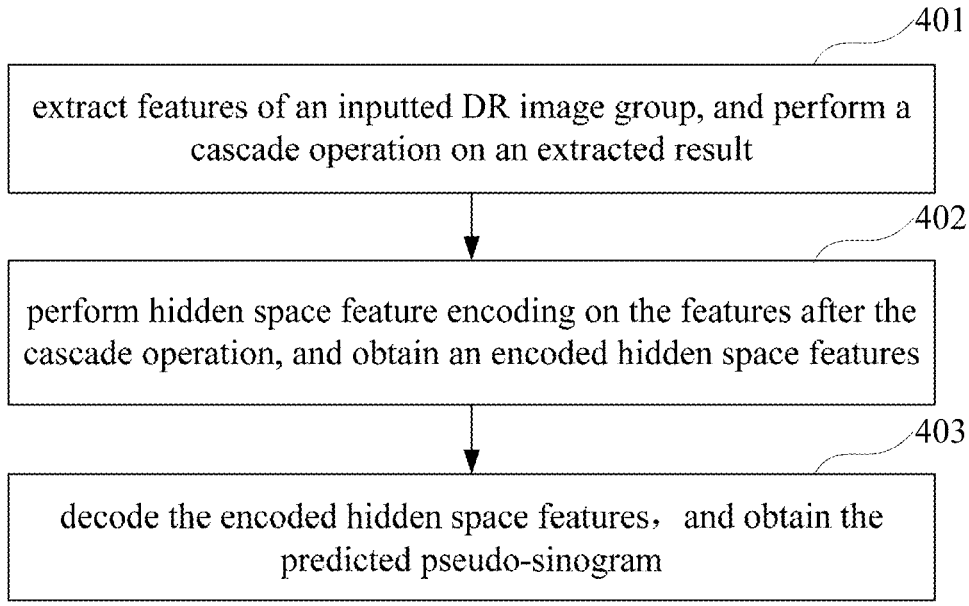

401 extract features of an inputted DR image group, and perform a cascade operation on an extracted result

402 perform hidden space feature encoding on the features after the cascade operation, and obtain an encoded hidden space features

403 decode the encoded hidden space features， and obtain the predicted pseudo-sinogram

Fig.4

THREE-DIMENSIONAL CT IMAGING METHOD AND APPARATUS

CROSS-REFERENCE TO RELATED DISCLOSURE

This disclosure claims priority to Chinese Patent Disclosure No. 202410831945.1, filed on Jun. 25, 2024, which is hereby incorporated herein by reference in its entirety.

FIELD

Embodiments of the disclosure relate to a three-dimensional CT imaging method and apparatus based on X-ray dual projection.

BACKGROUND

An X-ray computed tomography (CT) image is a three-dimensional radiological medical image reconstructed using digital geometric processing. To obtain three-dimensional CT images, the problem of three-dimensional volume reconstruction is usually solved first.

SUMMARY

In one aspect, a three-dimensional CT imaging method is provided by embodiments of the present disclosure, the method includes: collecting two DR images with a perpendicular relationship for an object to be imaged; inputting the two DR images into a preset three-dimensional volume reconstruction model to obtain a three-dimensional volume of the object outputted by the three-dimensional volume reconstruction model; and slicing the three-dimensional volume to obtain three-dimensional CT imaging of the object, wherein the preset three-dimensional volume reconstruction model is trained using multiple training samples, each training sample comprising: an input training sample, an intermediate training sample and an output training sample; the input training sample comprises a DR image group composed of two DR images with a perpendicular relationship, the intermediate training sample comprises a pseudo-sinogram corresponding to the DR image group, and the output training sample comprises a three-dimensional volume corresponding to the DR image group.

In another aspect, a method for generating a three-dimensional volume reconstruction model is provided by the embodiments of the present disclosure, the method includes: obtaining a training data set, wherein the training data set comprises DR images of reference objects collected circumferentially; obtaining multiple training samples based on the training data set, each training sample comprises: an input training sample, an intermediate training sample and an output training sample; the input training sample comprises a DR image group composed of two DR images with a perpendicular relationship, the intermediate training sample comprises a pseudo-sinogram corresponding to the DR image group, and the output training sample comprises a three-dimensional volume corresponding to the DR image group; and training a three-dimensional volume reconstruction model to be trained by using the multiple training samples to obtain a trained three-dimensional volume reconstruction model.

In yet another aspect, a three-dimensional CT imaging apparatus is provided by embodiments of the present disclosure, the apparatus includes: at least one memory, configured to store a preset three-dimensional volume reconstruction model and computer program, wherein the preset three-dimensional volume reconstruction model is trained using multiple training samples, each training sample comprising: an input training sample, an intermediate training sample and an output training sample; the input training sample comprises a DR image group composed of two DR images with a perpendicular relationship, the intermediate training sample comprises a pseudo-sinogram corresponding to the DR image group, and the output training sample comprises a three-dimensional volume corresponding to the DR image group; and at least one processor, configured to read the computer program and perform the following operations: collecting two DR images with a perpendicular relationship for an object to be imaged; inputting the two DR images into the preset three-dimensional volume reconstruction model to obtain a three-dimensional volume of the object outputted by the three-dimensional volume reconstruction model; and slicing the three-dimensional volumes to obtain three-dimensional CT imaging of the object.

As can be seen from the above technical solutions, a three-dimensional volume of an object to be imaged can be obtained by using two DR images with a perpendicular relationship through an established preset three-dimensional volume reconstruction model, and the three-dimensional volume can be sliced to obtain three-dimensional CT imaging of the object in the above embodiments. This solution can improve the speed of three-dimensional volume reconstruction on the basis of ensuring a quality of imaging, and then obtain high-quality three-dimensional CT imaging quickly.

BRIEF DESCRIPTION OF THE DRAWINGS

In order to explain technical solutions in embodiments of the present disclosure more clearly, the drawings to be used in the description of the embodiments will be briefly introduced below. Obviously, the drawings in the following description are merely some embodiments of the present disclosure. For those skilled in the art, other drawings can be obtained according to these drawings without creative work.

FIG. 1 is a schematic flow chart of three-dimensional CT imaging in accordance with some embodiments of the present disclosure.

FIG. 3A is a schematic flow chart illustrating a method for generating a preset three-dimensional volume reconstruction model in accordance with some embodiments of the present disclosure.

FIG. 3B is a schematic flow chart illustrating a method for training a three-dimensional volume reconstruction model in accordance with some embodiments of the present disclosure.

FIG. 4 is a schematic flow chart illustrating a method for obtaining a training pseudo-sinogram through an enhanced network model in accordance with some embodiments of the present disclosure.

DETAILED DESCRIPTION

Figures 2A, 2B:
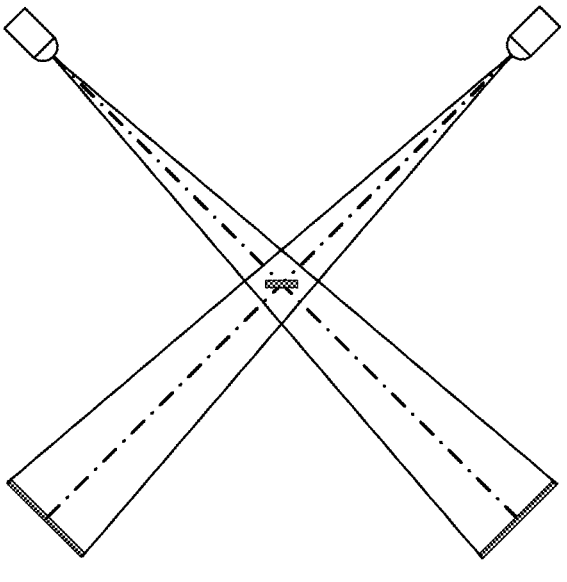
FIG. 2A is a schematic diagram of capturing dual projection angle DR images in accordance with some embodiments of the present disclosure.
FIG. 2B is a schematic diagram illustrating a method for obtaining a pseudo-sinogram based on 360 DR images in accordance with some embodiments of the present disclosure.

Hereinafter, technical solutions in embodiments of the present disclosure will be clearly and completely described with reference to the drawings in the embodiments of the present disclosure. Obviously, the described embodiments are only some of the embodiments of the present disclosure, but not all of the embodiments. All other embodiments obtained by those skilled in the art based on the embodiments in the present disclosure without creative work fall within the protection scope of the present disclosure.

The terms "first", "second", "third", "fourth", and the like (if any) in the description, the claims, and the drawings of the present disclosure are used to distinguish similar objects, and are not necessarily used to describe the order or sequence of the objects. It should be understood that data thus used are interchangeable under appropriate circumstances so that embodiments of the disclosure described herein can be implemented in other orders than those illustrated or described herein. Further, the terms "including" and "having" and any variations thereof are intended to cover non-exclusive inclusion. For example, a process, method, system, product, or device including a series of operations or units need not be limited to those explicitly listed but may include other operations or units not explicitly listed or inherent to the process, method, product, system, or apparatus.

Technical solutions of the present disclosure are described in detail with specific embodiments. The following specific embodiments can be combined with each other, and the same or similar concepts or processes may not be repeated in some embodiments.

To obtain three-dimensional CT imaging, the problem of three-dimensional volume reconstruction is usually solved first. The three-dimensional volume reconstruction methods in related art may include: using FDK and other algorithms for three-dimensional volume reconstruction, deep learning-based single projection three-dimensional volume reconstruction method, and the like. The method of using FDK and other algorithms for 3D volume reconstruction needs a large number of Digital Radiography (DR) images collected circumferentially.

The inventor finds that the related art has not been able to provide a technical scheme that can not only ensure the quality of imaging but also improve the speed of three-dimensional volume reconstruction, so that high-quality three-dimensional CT imaging cannot be obtained quickly.

Embodiments of the present disclosure propose an X-ray dual projection-based three-dimensional CT imaging method. With an established preset three-dimensional volume reconstruction model, two DR images with a perpendicular relationship can be used to obtain a three-dimensional volume of an object to be imaged, and the three-dimensional volume can be sliced to obtain three-dimensional CT imaging of the object. This technical solution can improve the speed of three-dimensional volume reconstruction on the basis of ensuring quality of imaging, and then obtain high-quality three-dimensional CT imaging quickly.

The object to be imaged for three-dimensional volume reconstruction and the reference objects for model training in an embodiment of the present disclosure may be various types of semiconductor devices and the like.

An X-ray dual projection-based three-dimensional CT imaging process in an embodiment of the present disclosure will be described in detail accompanied with the attached drawings.

Referring to FIG. 1, which is a schematic flow chart of the three-dimensional CT imaging method in some embodiments of the present disclosure, the specific operations are as follows.

Operation 101, collect two DR images with a perpendicular relationship for an object to be imaged.

In an embodiment of the present disclosure, when DR images are collected for the object, it is only necessary to collect two DR images with a perpendicular relationship, and it is not necessary to acquire 360 DR images at 360 degrees circumferentially. The two DR images with a perpendicular relationship refer to two DR images whose projection angles (or capturing angles) are perpendicular to each other. FIG. 2A shows a schematic diagram of capturing dual projection angle DR images in accordance with some embodiments. As shown in FIG. 2A, the capturing angles of the two DR images are perpendicular to each other.

Operation 102, input the two DR images into a preset three-dimensional volume reconstruction mode, and obtain a corresponding three-dimensional volume of the object outputted by the three-dimensional volume reconstruction mode.

The collected two DR images with a perpendicular relationship are inputted into the three-dimensional volume reconstruction model, and a three-dimensional volume of the object is outputted by the three-dimensional volume reconstruction mode.

The preset three-dimensional volume reconstruction model may be generated by the following operations: obtaining a training data set, where the training data set includes DR images of reference objects collected circumferentially; obtaining multiple training samples based on the training data set; and training a three-dimensional volume reconstruction model to be trained by using the multiple training samples to obtain the preset three-dimensional volume reconstruction model.

In some embodiments, each training sample may at least include an input training sample, and an output training sample corresponding to the input training sample. In the example, the input training sample may include a DR image group composed of two DR images with a perpendicular relationship, and the output training sample may include a three-dimensional volume corresponding to the DR image group.

Furthermore, in order to fully utilize the features of projection data, the concept of "pseudo-sinogram" is creatively proposed in some embodiments of the present disclosure when training a three-dimensional volume reconstruction model. Refer to FIG. 2B, which is a schematic diagram of obtaining a pseudo-sinogram based on 360 DR images in accordance with some embodiments of the present disclosure. As shown on the left side of FIG. 2B, for each reference object, the 360 DR images of the reference object are first stacked in a three-dimensional matrix in the order of capturing, with each layer being a sinogram; then the sinograms of all layers are added in columns and normalized to obtain the pseudo sinogram shown on the right side of FIG. 2B. It can be seen that the pseudo sinogram has regular feature details and a shape structure that is more conducive to learning. Therefore, it can be used as an intermediate training sample between the input training sample of the two-dimensional projection and the output training sample of the three-dimensional volume, which is more conducive to extracting effective features. Therefore, the pseudo sinogram is used as a soft transition from the two-dimensional DR images to the three-dimensional volume. At this point, each training sample may further include an intermediate training sample, which includes a pseudo sinogram corresponding to the DR image group.

Operation 103, slice the three-dimensional volume to obtain three-dimensional CT imaging of the object.

How to obtain the three-dimensional CT imaging by slicing one three-dimensional volume is not limited in the embodiment of the present disclosure.

A three-dimensional volume of an object to be imaged can be obtained by using two DR images with a perpendicular relationship through an established preset three-dimensional volume reconstruction model, and three-dimensional CT imaging of the object can be obtained by slicing the three-dimensional volume in the embodiment of the present disclosure. This technical solution can improve a speed of three-dimensional volume reconstruction on the basis of ensuring a quality of imaging, and then obtain high-quality three-dimensional CT imaging quickly.

The process of generating a three-dimensional volume reconstruction model in an embodiment of the present disclosure is given in detail in conjunction with the drawings below.

Referring to FIG. 3A, which is a schematic flow chart illustrating a method for generating a preset three-dimensional volume reconstruction model in accordance with some embodiments of the disclosure, the specific processes may be as follows.

Operation 301, obtain a training data set, where the training data set includes DR images, of each of reference objects, captured circumferentially.

The obtained training data set may be a pre-stored data set or a collected data set.

The method for collecting a training data set may be implemented as follows.

DR images of each of semiconductor devices (reference objects) of various types of defects may be captured circumferentially. DR images collected for each semiconductor device may be 360 DR images in different directions.

During a collection process, relevant parameters such as tube voltage, tube current, exposure time, and position during a period under test are kept unchanged.

The collected DR images may be preprocessed first, and the preprocessing may include: performing processing such as sizing and cropping, taking a logarithm, and normalization on the collected DR images based on a chip parameter and a mechanical parameter.

Operation 302, obtain a reference three-dimensional volume and a reference pseudo-sinogram of each of the reference objects based on the training data set.

The obtaining of the reference three-dimensional volume of each of the reference objects may include: for each reference object, obtaining a reference three-dimensional volume of the reference object based on the 360 DR images of the reference object using a mature algorithm such as FDK.

The obtaining of the reference pseudo-sinogram of each of the reference objects may include: for each reference object, stacking the 360 DR images of the reference object in a three-dimensional matrix in the capturing order, where each layer is a sinogram at this time; and adding the sinograms of all layers in columns and normalizing added sinograms to obtain a pseudo-sinogram.

Operation 303, divide the DR images of each of the reference objects in the training data set into a plurality of DR image groups, where each of the DR image groups includes two DR images with a perpendicular relationship.

Operation 304, associate each DR image group with a reference pseudo-sinogram and a reference three-dimensional volume corresponding to the same reference object to obtain a corresponding training sample.

The plurality of DR image groups of the same reference object corresponds to one reference three-dimensional volume and one pseudo-sinogram, namely, each reference object corresponds to a plurality of DR image groups, one reference pseudo-sinogram, and one reference three-dimensional volume. Each DR image group can be associated with one reference pseudo-sinogram and one reference three-dimensional volume through the reference object in the embodiment, each DR image group may be used as an input training sample, and the reference three-dimensional volume associated with the DR image group may be used as the output training sample corresponding to the input training sample. The reference pseudo sinogram associated with the DR image group can be used as the intermediate training sample corresponding to the input training sample and the output training sample. Here, the input training sample, output training sample, and intermediate training sample form a training sample.

Operation 305, train the three-dimensional volume reconstruction model to be trained using the training samples to obtain a trained three-dimensional volume reconstruction model. The trained three-dimensional volume reconstruction model may be taken as the preset three-dimensional volume reconstruction model.

In the embodiment, the three-dimensional volume reconstruction model to be trained may be constructed based on convolutional neural networks, and the constructed three-dimensional volume reconstruction model includes an input, an intermediate output, and a final output. During specific training, the input training sample in each training sample can be used as an input for the three-dimensional volume reconstruction model to be trained, the corresponding intermediate training sample may be used as an intermediate standard output for the three-dimensional volume reconstruction model, and the corresponding output training sample may be used as a final standard output for the three-dimensional volume reconstruction model.

In some embodiments, the training process in operation 305 may include the following operations shown in FIG. 3B. FIG. 3B is a schematic flow chart illustrating a method for training a three-dimensional volume reconstruction model in accordance with some embodiments of the present disclosure.

Operation 3051, for each training sample, input the DR image group in the training sample into the three-dimensional volume reconstruction model, and obtain a predicted pseudo-sinogram and a predicted three-dimensional volume outputted by the three-dimensional volume reconstruction model.

The three-dimensional volume reconstruction model in the embodiment of the present disclosure may include a feature-enhanced network model and a reconstruction network model, where the enhanced network model may be a modal based on the network architecture of an encoder and a decoder and may be used to input a DR image group including two DR images with a perpendicular relationship and output a corresponding predicted pseudo-sinogram; and the reconstruction network model may be a self-encoder network model with two-dimensional DR images to three-dimensional volume mapping and may be used to input a predicted pseudo-sinogram and output a corresponding predicted three-dimensional volume.

Refer to FIG. 4, which is a schematic flow chart illustrating a method for obtaining a training pseudo-sinogram through an enhanced network model in accordance with some embodiments of the present disclosure, and the specific processes may be as follows.

Operation 401, extract features of an inputted DR image group, and perform a cascade operation on an extracted result.

Operation 402, perform hidden space feature encoding on the features after the cascade operation, and obtain encoded hidden space features.

Operation 403, decode the encoded hidden space features and obtain the predicted pseudo-sinogram.

In specific implementation, the extraction of a feature of each DR image in the inputted DR image group can be achieved through at least one for example three dense residual blocks, and the hidden space feature encoding of the feature after the cascade operation can be achieved by an encoder including at least one for example four down-samplers. Decoding the encoded hidden space feature to obtain the predicted pseudo-sinogram can be achieved by a decoder including at least one for example four up-samplers, and at the same time, the training pseudo-sinogram can be obtained finally by utilizing a residual link to play the role of linking contextual information.

Figure 5:
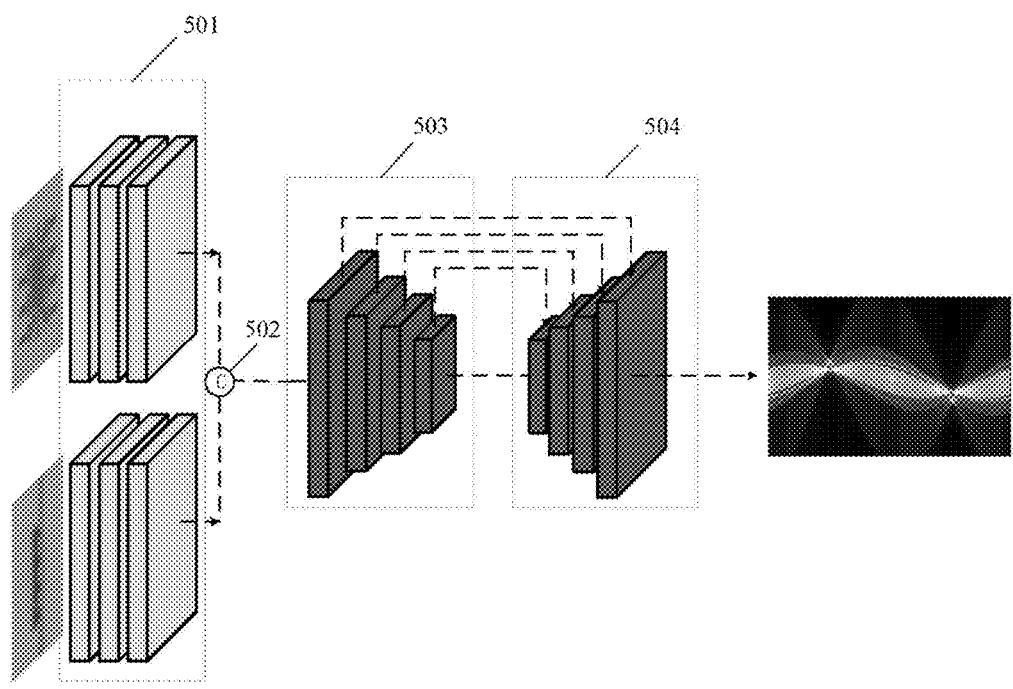
FIG. 5 is a schematic diagram illustrating a structure of the enhanced network model in accordance with some embodiments of the present disclosure.

Referring to FIG. 5, which is a schematic diagram illustrating the structure of an enhanced network model in accordance with some embodiments of the present disclosure, the enhanced network model in FIG. 5 receives and processes two DR images in an inputted DR image group respectively by two groups of dense residual blocks 501 and then performs the operation of cascade unit 502. Each of the two groups of dense residual blocks 501 receives and processes one DR image in the DR image group, and each of the two groups of dense residual blocks 501 may include at least one dense residual block, and three dense residual blocks are shown as an example in FIG. 5, In the example, a feature is extracted from the corresponding DR image using the three dense residual blocks, and then a cascade operation is performed on the extraction results of the two groups of dense residual blocks 501 to fuse and share the features of the two DR images. In the embodiment, the original information is preserved and the features are enhanced through the two groups of dense residual blocks 501 and the operation of cascade unit 502.

In some embodiments, the number of feature channels for each dense residual block may be 1 and remain unchanged.

Next, the enhanced features are inputted into an encoder 503 including at least one for example four down-sampling modules, and the hidden space feature encoding of the features may be achieved through encoding processing of the encoder. At this time, the input data is mapped to a low-dimensional space, and a main feature remains under the condition of keeping the number of feature channels unchanged so that the extracted information for example spatial information and global information can be used for accurate reconstruction. The spatial information refers to the relative positional relationships between pixels in an image and the features of local regions. The global information refers to the overall features and contextual information of an image.

The encoded hidden space features outputted by the encoder are inputted into a decoder 504, which is used to decode the hidden space features to obtain a corresponding predicted pseudo-sinogram. The decoder includes at least one up-sampling module, and four up-sampling modules are shown as an example in FIG. 5. The four up-sampling modules are configured to perform an up-sampling operation, and at the same time, by making use of a residual link playing the role of linking contextual information, the spatial dimension is gradually restored to original set data spatial resolution to obtain the corresponding predicted pseudo-sinogram, where the original set data spatial resolution may be the spatial resolution of the reference pseudo-sinogram.

Figure 6:
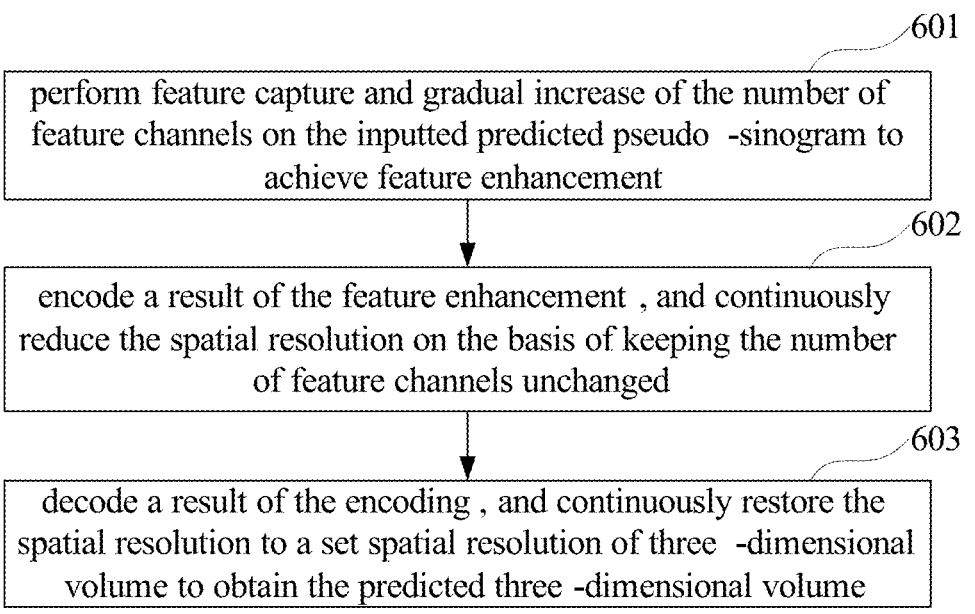
FIG. 6 is a schematic flow chart illustrating a method for obtaining a training three-dimensional volume through a reconstruction network model in accordance with some embodiments of the present disclosure.

Referring to FIG. 6, which is a schematic flow chart illustrating a method for obtaining a predicted three-dimensional volume through a reconstruction network model in accordance with some embodiments of the present disclosure, the specific operations are as follows.

Operation 601, perform feature capture and gradual increase of the number of feature channels on the inputted predicted pseudo-sinogram to achieve feature enhancement.

Operation 602, encode a result of the feature enhancement, and continuously reduce the spatial resolution on the basis of keeping the number of feature channels unchanged.

Operation 603, decode a result of the encoding and continuously restore the spatial resolution to a set spatial resolution of three-dimensional volume to obtain the predicted three-dimensional volume. The set spatial resolution may be a spatial resolution of the reference three-dimensional volume.

In a specific implementation, feature capture and gradual increase of the number of feature channels are performed on the inputted predicted pseudo-sinogram by at least one, for example, three dense residual blocks to achieve the feature enhancement, encoding a result of the feature enhancement can be achieved by an encoder including at least one, for example, four down-samplers, and decoding a result of the encoding can be achieved by a decoder including at least one, for example, four up-sampling.

The number of dense residual blocks can be configured according to the requirements of the three-dimensional volume for the number of feature channels and the granularity of channel enhancement. For example, in a case that a three-dimensional volume requires 128 feature channels, namely the number of channels needs to be increased from 1 to 128, in an example, three dense residual blocks may be set, and the number of channels may be sequentially increased from 1 to 2 through the first dense residual block, from 2 to 64 through the second dense residual block, and from 64 to 128 through the third dense residual block. In another example, six dense residual blocks may be set, and the number of channels may be sequentially increased from 1 to 2 through the first dense residual block, from 2 to 8 through the second dense residual block, from 8 to 16 through the third dense residual block, from 16 to 32 through the fourth dense residual block, from 32 to 64 through the fifth dense residual block, and from 64 to 128 through the sixth dense residual block. In other examples, other numbers of dense residual blocks may also be set, which will not be listed one by one here.

Figure 7:
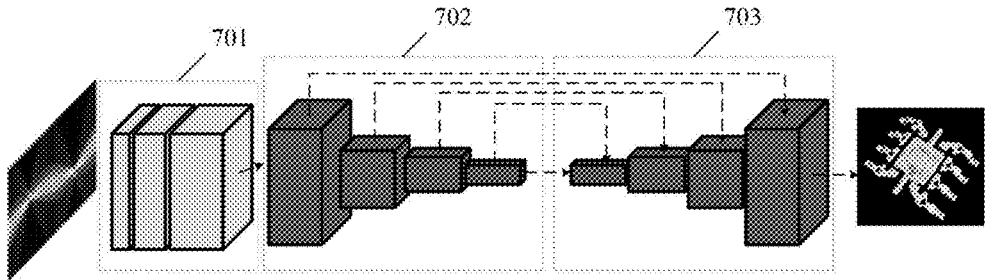
FIG. 7 is a schematic diagram illustrating a structure of the reconstruction network model in accordance with some embodiments of the present disclosure.

Referring to FIG. 7, which is a schematic diagram illustrating the structure of a reconstruction network model in accordance with some embodiments of the present disclosure. First, the reconstruction network model in FIG. 7 receives and processes the inputted predicted pseudo-sinogram through a group of dense residual blocks 701, which includes at least one dense residual block, and three dense residual blocks are shown as an example in FIG. 7, feature capture and gradual increase of the number of feature channels are implemented through these three dense residual blocks to achieve feature enhancement. Because the feature output of each channel in the group of dense residual blocks is directly related to an intermediate feature map, feature extraction in a deep neural network has a significant advantage. During this processing, the spatial resolution is kept constant and the number of channels is continuously increased.

Then, a result of the feature enhancement is inputted into an encoder 702 including at least one for example four down-sampling modules. At this time, the number of channels is kept constant and the spatial resolution is continuously reduced. At this stage, the features are better expressed.

Finally, a result of the encoding is decoded by a decoder 703 including at least one for example four up-sampling modules, and the spatial resolution is continuously restored to the spatial resolution of the reference three-dimensional volume, and finally, the predicted three-dimensional volume is obtained.

Figure 8A:
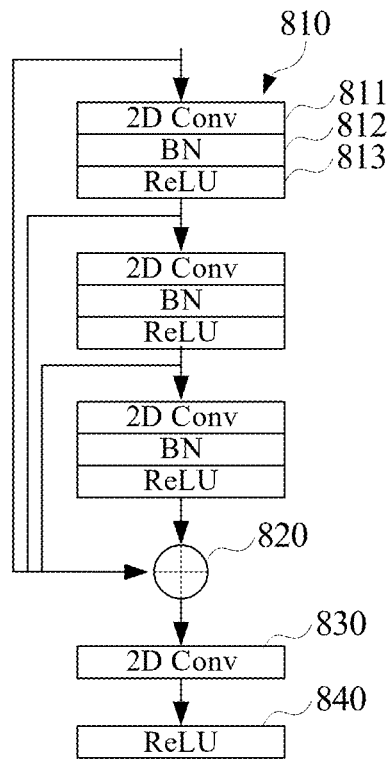
FIG. 8A is a schematic diagram of a dense residual block in accordance with some embodiments of the present disclosure.

FIG. 8A is a schematic diagram of a dense residual block in accordance with some embodiments of the present disclosure. As shown in FIG. 8A, a dense residual block may include at least two layers of operation units 810, and three layers of operation units are shown as an example in FIG. 8A, Each layer of operation units may include a two-dimensional convolution (2D Conv) 811, a two-dimensional batch normalization (BN) 812, and a ReLU activation function 813. Afterward, an input of each layer of the operation unit and an output of the third layer (namely the last layer) of the operation unit are cascaded by a cascade unit 820, and then a two-dimensional convolution processing and a ReLU activation processing is applied to a cascaded operation result respectively by a two-dimensional convolution 830 and a ReLU activation function 840. By using dense residual blocks and creating dense connections between each layer of the operation unit, feature representation may be improved, thereby enhancing the flow of information (such as gradients) in the network and achieving better parameter efficiency. Among them, dense connections have significant advantages in feature extraction because each channel feature outputted by the dense connections is directly associated with the intermediate feature map, allowing for the preservation of detailed information in each feature map.

Figure 8B:
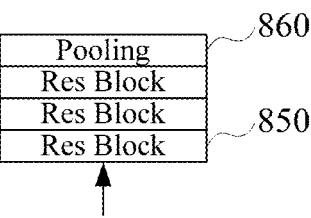
FIG. 8B is a schematic diagram of a down-sampling module in accordance with some embodiments of the present disclosure.

FIG. 8B is a schematic diagram of a down-sampling module in accordance with some embodiments of the present disclosure. As shown in FIG. 8B, each down-sampling module includes at least one, for example, three residual blocks 850, and a maximum pooling layer 860, so that the spatial resolution will be half of the original. The residual blocks 850 here may be ordinary residual blocks or dense residual blocks.

Figure 8C:
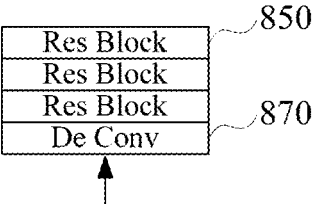
FIG. 8C is a schematic diagram of an up-sampling module in accordance with some embodiments of the present disclosure.

FIG. 8C is a schematic diagram of an up-sampling module in accordance with some embodiments of the present disclosure. As shown in FIG. 8C, each up-sampling module includes a de-convolution (also known as transposed convolution, or fractionally strided convolution) layer 870 and at least one, for example, three residual blocks 850, which doubles the spatial resolution. The residual blocks 850 here may be ordinary residual blocks or dense residual blocks.

Operation 3052, calculate a loss value based on the predicted pseudo-sinogram, the predicted three-dimensional volume, the reference pseudo-sinogram, and the reference three-dimensional volume in the training sample, to enable the three-dimensional volume reconstruction model to be reverse optimized based on the loss value.

For each DR image group, a corresponding predicted pseudo-sinogram and predicted three-dimensional volume will be obtained when the DR image group is inputted into the three-dimensional volume reconstruction model. The loss value is calculated based on the obtained predicted pseudo-sinogram and predicted three-dimensional volume, and the reference three-dimensional volume and reference pseudo-sinogram corresponding to the DR image group.

In a specific implementation, the number of DR image groups that are inputted into the three-dimensional volume reconstruction model each time is not limited, that is, whether parallel processing or serial processing is to be performed is determined by equipment capacity.

No matter how DR image groups are inputted, in some embodiments of the present disclosure, a loss value corresponding to a DR image group is directly calculated every time a predicted pseudo-sinogram and a predicted three-dimensional volume are obtained for the DR image group.

The specific process of calculating the loss value may include: calculating the loss value using a preset loss function based on the predicted pseudo-sinogram, the predicted three-dimensional volume, the reference three-dimensional volume, and the reference pseudo-sinogram, where the preset loss function may be a function of a weighted sum of a first loss function and a second loss function.

The first loss function is configured to calculate a mean square error loss of a predicted pseudo-sinogram and a reference pseudo-sinogram;

The second loss function is configured to calculate a mean square error loss of a predicted three-dimensional volume and a reference three-dimensional volume.

The Mean Squared Error (MSE) loss function is used to calculate the difference between input data and reconstructed data of a model, and the calculation formula is as follows:

$$MSE(y_i, \hat{y}_i) = \frac{1}{n} \sum_{i=1}^{n} (y_i - \hat{y}_i)^2,$$

where, n is the total number of data points, $y_i$ is the i-th actual observation value, and $\hat{y}_i$ is the i-th predicted value.

Based on the mean square error loss, the preset loss function in an embodiment of the present disclosure may be expressed as:

a×loss_1+b×loss_2, where, loss_1=MSE (S, Ŝ) denotes the first loss function, S denotes the reference pseudo-sinogram, and Ŝ denotes the predicted pseudo-sinogram; loss_2=MSE (V, V̂) denotes the second loss function, V denotes the reference three-dimensional volume, and V̂ denotes the predicted three-dimensional volume; and a and b denotes weighted values, and may also be called proportional coefficients.

In the embodiment of the disclosure, before the training is completed, the three-dimensional volume reconstruction model is reversely optimized based on the loss value calculated each time to gradually reduce the loss value and complete the training.

Operation 3053, terminate the training and obtain the preset three-dimensional volume reconstruction model, in a case that any loss value calculated is less than a target loss value or the training times reach a target number of times.

One loss value is obtained for each DR image group in a training sample, and once the loss value of a DR image group is less than the target loss value, the training is terminated.

In a case that the loss value less than the target loss value has not been obtained always, but the times of training reach the target number of times, the training may also be terminated.

In a specific implementation, in a case that the loss value less than the target loss value has not been obtained always, the target loss value may be set to be too small or the initial parameters of the model are set unreasonably, and at this time the training needs to be terminated. It may be directly considered that the model has completed the training, or the parameters may be set again for training. In an embodiment of the present disclosure, it is taken as an example that the initial parameters set for the training are already the most reasonable parameters, the preset three-dimensional volume reconstruction model may be directly determined when the training is ended.

A concept of pseudo-sinogram is proposed in embodiments of the present disclosure to be used to train a model. The proposed pseudo-sinogram has regular feature details and a shape structure that is more conducive to learning and is transformed into a supervision of an intermediate operation from two-dimensional projection to three-dimensional volume, which is more conducive to the effective characterization of extracted features. Using a pseudo-sinogram as a soft transition from two-dimensional data to three-dimensional volume can reconstruct a cross-latitude generation network with high detail accuracy, and then establish a preset three-dimensional volume reconstruction model with high accuracy. Further, the accuracy of the obtained three-dimensional volume is ensured.

And, in an embodiment of the present disclosure, a method of dual viewing angles (two DR images with perpendicular directions) is adopted to improve the speed of three-dimensional volume reconstruction on the basis of ensuring the quality of imaging, and then quickly obtain high-quality three-dimensional CT imaging.

All the above optional technical solutions may be combined in any way to form an optional embodiment of the present disclosure, and they will not be repeated here.

The three-dimensional CT imaging method and the method for generating a three-dimensional volume reconstruction model in embodiments of the disclosure are described in detail above, and the three-dimensional CT imaging apparatus and the apparatus for generating a three-dimensional volume reconstruction model in embodiments of the disclosure are described in detail below. The apparatus embodiments of the disclosure can be used to implement the corresponding method embodiments. For details not disclosed in apparatus embodiments of the disclosure, please refer to the corresponding description in method embodiments of the disclosure.

Figure 9:
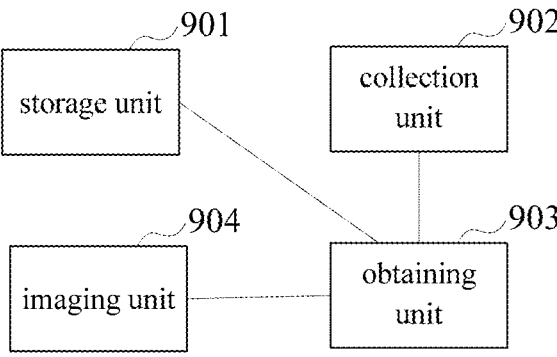
FIG. 9 is a schematic diagram illustrating a structure of an X-ray dual projection-based three-dimensional CT imaging apparatus in accordance with some embodiments of the present disclosure.

Based on the same inventive concept, an embodiment of the present disclosure also provides a three-dimensional CT imaging apparatus. Referring to FIG. 9, which is a schematic diagram illustrating a structure of the three-dimensional CT imaging apparatus in accordance with some embodiments of the present disclosure, the apparatus may include: a storage unit 901, a collection unit 902, an obtaining unit 903, and an imaging unit 904.

The storage unit 901 is configured to store a preset three-dimensional volume reconstruction model, where the preset three-dimensional volume reconstruction model is generated by: obtaining a training data set, where the training data set includes DR images of reference objects collected circumferentially; obtaining multiple training samples based on the training data set; and training a three-dimensional volume reconstruction model to be trained by using the multiple training samples to obtain the preset three-dimensional volume reconstruction model.

In some embodiments, each training sample may include an input training sample, an intermediate training sample, and an output training sample corresponding to the input training sample. In the example, the input training sample may include a DR image group composed of two DR images with a perpendicular relationship, the intermediate training sample may include a pseudo sinogram corresponding to the DR image group; and the output training sample may include a three-dimensional volume corresponding to the DR image group.

In an example, the storage unit 901 may include at least one storage.

The collection unit 902 is configured to collect two DR images with a perpendicular relationship for an object to be imaged. In an example, the collection unit 902 may include an X-ray tube and a detector. In another example, the collection unit 902 may also be a program module stored in the storage unit 901, and configured to obtain two DR images, of the object to be imaged, with a perpendicular relationship captured by an acquisition device when executed by a processor. In an example, the acquisition device may include the X-ray tube and the detector.

The obtaining unit 903 is configured to input the two DR images into a preset three-dimensional volume reconstruction mode and obtain a corresponding three-dimensional volume of the object outputted by the three-dimensional volume reconstruction model. In an example, the obtaining unit 903 may be a program module stored in the storage unit 901, and configured to input the two DR images with perpendicular relationships into the preset three-dimensional volume reconstruction model when executed by a processor and obtain the three-dimensional volume of the object to be imaged outputted by the three-dimensional volume reconstruction model.

The imaging unit 904 is configured to perform slicing on the three-dimensional volume to obtain three-dimensional CT imaging of the object. In an example, the imaging unit 904 may be a program module stored in the storage unit 901, and configured to slice the three-dimensional volume when executed by a processor to obtain a three-dimensional CT image of the object to be imaged.

Figure 10:
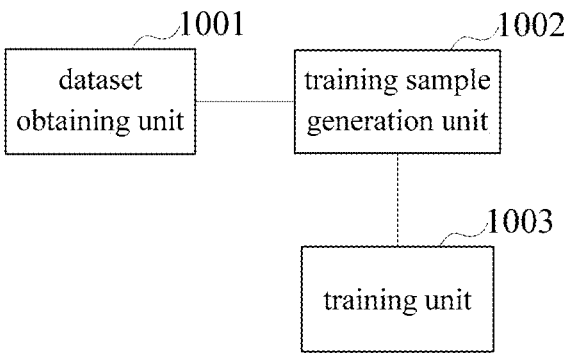
FIG. 10 is a schematic diagram illustrating an apparatus for generating a three-dimensional volume reconstruction model in accordance with some embodiments of the present disclosure.

The embodiments of the present disclosure also provide a three-dimensional volume reconstruction model generation apparatus. In an example, the aforementioned three-dimensional volume reconstruction model may be generated using the three-dimensional volume reconstruction model generating apparatus. Refer to FIG. 10, which is a schematic diagram of the structure of the apparatus for generating the three-dimensional volume reconstruction model in accordance with some embodiments of the present disclosure. The apparatus may include: a dataset obtaining unit 1001, a training sample generation unit 1002, and a training unit 1003.

The dataset obtaining unit 1001 is configured to obtain a training data set. In an example, the dataset obtaining unit 1001 may be a collector, or may be a program module stored in a storage unit.

The training sample generation unit 1002 is configured to generate multiple training samples based on the training data set.

In an example, the training sample generation unit 1002 may obtain a reference three-dimensional volume and a reference pseudo-sinogram of each of the reference objects based on the training data set; when acquiring the training data set, the reference pseudo-sinogram may be obtained by stacking collected DR images of a same reference object in a three-dimensional matrix in the collection order, adding the sinograms in all layers in columns, and normalizing added sinograms; dividing the DR images of each of the reference objects in the training data set into a plurality of DR image groups, where each of the DR image groups includes two DR images with a perpendicular relationship. For each reference object, associate each DR image group of the reference object with the reference three-dimensional volume and reference pseudo-sinogram of the reference object to obtain a training sample. In one example, the training sample generation unit 1002 may be a computing circuit or a program module stored in a memory.

The training unit 1003 is configured to train the three-dimensional volume reconstruction model using the multiple training samples, and obtain the preset three-dimensional volume reconstruction model. In an example, the training unit 1003 may be a training circuit or a program module stored in a memory.

To be specific, the training unit 1003 may input the DR image group in each training sample into the three-dimensional volume reconstruction model to be trained, and obtain a predicted pseudo-sinogram and a predicted three-dimensional volume outputted by the three-dimensional volume reconstruction model; calculate a loss value based on the predicted pseudo-sinogram, the predicted three-dimensional volume, the reference pseudo-sinogram and the reference three-dimensional volume in the training order; terminate the training, thereby obtaining the preset three-dimensional volume reconstruction model, in a case that any loss value calculated is less than a target loss value or the training times reaches a target number of times.

In an example, the three-dimensional volume reconstruction model may include a feature-enhanced network model and a reconstruction network model.

The enhanced network model may be a model based on a network architecture of an encoder and a decoder and is configured to input a DR image group with a perpendicular relationship and output a corresponding predicted pseudo-sinogram.

The reconstruction network model may be a self-encoder network model with two-dimensional to three-dimensional volume mapping and is configured to input a predicted pseudo-sinogram and output a corresponding predicted three-dimensional volume.

In an example, the enhanced network model may extract features of the inputted DR image group, and perform a cascade operation on the results of the extraction; perform hidden space feature encoding on the features after the cascade operation and obtain encoded hidden space features; and decode the encoded hidden space features and obtain the predicted pseudo-sinogram.

In an example, the reconstruction network model may perform feature capture and gradual increase of the number of feature channels on the inputted predicted pseudo-sinogram to achieve the feature enhancement; encode a result of the feature enhancement, and continuously reduce the spatial resolution on the basis of keeping the number of channels unchanged; and decode a result of the encoding, and continuously restore the spatial resolution to a spatial resolution of the reference three-dimensional volume to obtain the predicted three-dimensional volume.

In an example, the training unit 1003 may calculate a loss value using a preset loss function based on the predicted pseudo-sinogram, the predicted three-dimensional volume, the reference three-dimensional volume, and the reference pseudo-sinogram, where the preset loss function is a function of a weighted sum of a first loss function and a second loss function, the first loss function is configured to calculate a mean square error loss of a predicted pseudo-sinogram and a reference pseudo-sinogram; and the second loss function is configured to calculate a mean square error loss of a predicted three-dimensional volume and a reference three-dimensional volume.

The units of the above embodiments may be integrated into one body or deployed separately and may be combined into one unit or may be further split into a plurality of sub-units.

In another embodiment, there is also provided an electronic device including a memory, a processor, and a computer program stored on the memory and executable on the processor, the processor implementing an X-ray dual projection based three-dimensional CT imaging method when executing the program.

In another embodiment, there is also provided a computer-readable storage medium having stored thereon computer instructions which, when executed by a processor, carry out a three-dimensional CT imaging method mentioned above, or carry out a method for generating the three-dimensional volume construction model.

Figure 11:
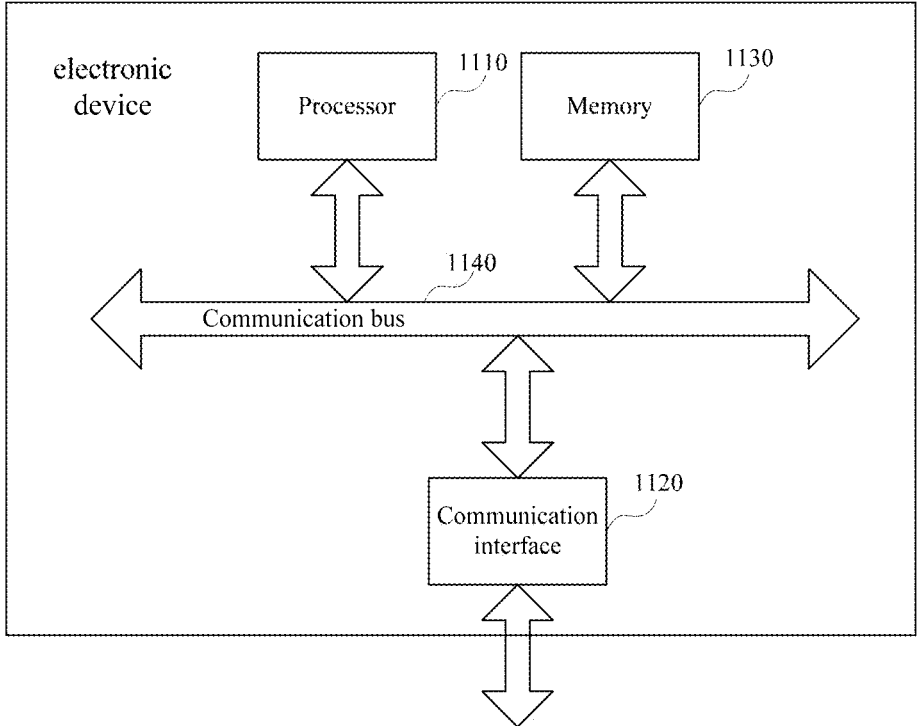
FIG. 11 is a schematic diagram illustrating a structure of an electronic device in accordance with some embodiments of the present disclosure.

FIG. 11 is a schematic diagram illustrating the structure of an electronic device in accordance with some embodiments of the present disclosure. As shown in FIG. 11, the electronic device may include a processor 1110, a communication interface 1120, a memory 1130, and a communication bus 1140, where the processor 1110, the communication interface 1120, and the memory 1130 communicate with each other through the communication bus 1140. In an example, the processor 1110 may call the computer program in the memory 1130 to perform the three-dimensional CT imaging method shown in FIG. 1, in this case, the computer program may include the collection unit 902, the obtaining unit 903 and the imaging unit 904 shown in FIG. 9, and the memory 1130 may include the storage unit 901. In another example, the processor 1110 may call computer program in the memory 1130 to perform the method for generating a three-dimensional volume reconstruction model shown in FIG. 3, in this case, the computer program may include the dataset obtaining unit 1001, the training sample generation unit 1002, and the training unit 1003 shown in FIG. 10.

In addition, the computer program in the above-mentioned memory 1130 may be realized in the form of a software functional unit and may be stored in a computer-readable storage medium when sold or used as an independent product. Based on this understanding, a substantial part, a part making contribution over the prior art, or a part of a technical solution of the present disclosure can be embodied in the form of a software product, which is stored in a storage medium and includes several instructions to cause a computer device (which can be a personal computer, a server, or a network device, etc.) to execute all or part of the operations of the methods of various embodiments of the present disclosure. Further, the aforementioned storage medium includes various media that can store program code such as a USB drive, mobile hard disk, Read-Only Memory (ROM), Random Access Memory (RAM), magnetic disk, or optical disk.

The embodiments for apparatuses described above are merely illustrative, in which the units described as separate components may or may not be physically separated, and the components shown as units may or may not be physical units and may be located in one place or distributed to a plurality of network units. Some or all of the modules may be selected according to actual needs to achieve the purpose of the solution of an embodiment. Those skilled in the art can understand and implement it without creative work.

From the description of the above embodiments, those skilled in the art may clearly understand that each embodiment can be realized by means of software and a necessary general hardware platform, and of course, can also be realized by hardware. Based on this understanding, a substantial part or a part making contribution over the prior art of the above technical solution can be embodied in the form of a software product, which can be stored in a computer-readable storage medium, such as a ROM/RAM, magnetic disk, optical disk, etc., and includes several instructions to cause a computer device (which can be a personal computer, a server, or a network device, etc.) to execute the methods described in various embodiments or some parts of the embodiments.

The flowcharts and block diagrams in the drawings of the present disclosure show the architecture, functions, and operations of possible implementations of systems, methods, and computer program products according to various embodiments disclosed in the present disclosure. In this regard, each operation in the flowchart or block diagram may represent a module, a program segment, or a part of code, which contains one or more executable instructions for implementing a specified logical function. It should also be noted that in some alternative implementations, a function indicated in an operation may also occur in an order indicated in a different figure. For example, two continuously indicated operations may actually be executed substantially in parallel, and may sometimes be executed in a reverse order, depending on the function involved. It should also be noted that each operation in the block diagram or flowchart and combinations of operations in the block diagram or flowchart can be realized by a dedicated hardware-based system that performs a specified function or operation or can be realized by a combination of dedicated hardware and computer instructions.

It can be understood by those skilled in the art that the features described in various embodiments and/or claims disclosed in the present disclosure can be combined in various ways, even if such combinations are not explicitly described in the present disclosure. In particular, the features described in various embodiments and/or claims of the present disclosure can be combined in various ways without departing from the spirit and teaching of the present disclosure, and all these combinations fall within the scope of the present disclosure.

Specific embodiments are applied herein to explain the principle and implementation of the invention. The description of the above embodiments is only used to help understand the method and core idea of the invention and is not used to limit the present disclosure. For those skilled in the art, changes can be made in the specific implementation and disclosure scope according to the idea, spirit, and principle of the invention, and any modification, equivalent substitution, improvement, etc. made by them should be included in the protection scope of the present disclosure.

The invention claimed is:

1. A three-dimensional computed tomography (CT) imaging method based on X-ray dual projection, comprising:
   collecting two digital radiography (DR) images with a perpendicular relationship for an object to be imaged;
   obtain a three-dimensional volume of the object to be imaged corresponding to the two DR images with a perpendicular relationship based on a preset three-dimensional volume reconstruction model; and
   slicing the three-dimensional volume to obtain three-dimensional CT imaging of the object to be imaged,
   wherein, generating the preset three-dimensional volume reconstruction model comprises:
   obtaining a training data set; wherein the training data set is composed of DR images of reference objects collected circumferentially;
   training to-be-trained three-dimensional volume reconstruction model using DR images with a perpendicular relationship in the training data set to obtain the preset three-dimensional volume reconstruction model;
   wherein, when obtaining the training data set, the method further comprises:
   obtaining a reference three-dimensional volume and a reference pseudo-sinogram of each of the reference objects based on the training data set; wherein the reference pseudo-sinogram is obtained by stacking collected DR images of a same reference object into a three-dimensional matrix according to a collection order, summing sinograms in each layer column by column, and normalizing a sum result;
   dividing the DR images of each reference object in the training data set into a plurality of DR image groups, and each of the DR image groups comprises two DR images with a perpendicular relationship;
   wherein the training to-be-trained three-dimensional volume reconstruction model using DR images with a perpendicular relationship in the training data set to obtain the preset three-dimensional volume reconstruction model comprises:
   inputting the plurality of DR image groups into the to-be-trained three-dimensional volume reconstruction model, training the to-be-trained three-dimensional volume reconstruction model, and respectively obtaining a training pseudo-sinogram and a training three-dimensional volume;
   calculating a loss value based on the training pseudo-sinogram, the training three-dimensional volume, the reference pseudo-sinogram and the reference three-dimensional volume according to a training order;
   terminating the training and obtaining the preset three-dimensional volume reconstruction model in a case that any calculated loss value is less than a target loss value, or the number of training times reaches a target number of times.

2. The method according to claim 1 wherein the to-be-trained three-dimensional 1 volume reconstruction model comprises an enhancement network model and a reconstruction network model;

the enhancement network model is a model based on an encoder-decoder network architecture, and configured to input a DR image group with a perpendicular relationship and output a corresponding training pseudo-sinogram; and the reconstruction network model is an autoencoder network model for two-dimensional to three-dimensional volume mapping and configured to input the training pseudo-sinogram and output a corresponding training three-dimensional volume.

3. The method according to claim 2, wherein the enhancement network model to input a DR image group with a perpendicular relationship, and output a corresponding training pseudo-sinogram, comprises:

performing pattern and feature extraction on the inputted DR image group, and performing a cascade operation on a results of the extraction;

performing latent space feature encoding on features after the cascade operation to obtain encoded latent space features; and decoding the encoded latent space features to obtain the training pseudo-sinogram.

4. The method according to claim 2, wherein the reconstruction network model to input the training pseudo-sinogram, and output a corresponding training three-dimensional volume, comprises:

performing feature capture and enhancement on the input training pseudo-sinogram;

encoding a result of feature enhancement, and continuously reducing the spatial resolution on the basis of keeping the number of channels unchanged; and decoding a result of the encoding, and continuously restoring the spatial resolution to a spatial resolution of the reference three-dimensional volume to obtain the training three-dimensional volume.

5. The method according to claim 1, wherein the calculating a loss value based on the training pseudo-sinogram, the training three-dimensional volume, the reference pseudo-sinogram, and the reference three-dimensional volume according to the training order, comprises:

calculating the loss value using a preset loss function based on the training pseudo-sinogram, the training three-dimensional volume, the reference pseudo-sinogram, and the reference three-dimensional volume, wherein the preset loss function is a function of a weighted summation of a first loss function and a second loss function; the first loss function is configured to calculate a mean square error loss between a training pseudo-sinogram and a reference pseudo-sinogram, and the second loss function is configured to calculate a mean square error loss of a training three-dimensional volume and a reference three-dimensional volume.

6. The method according to claim 2, wherein the calculating a loss value based on the training pseudo-sinogram, the training three-dimensional volume, the reference pseudo-sinogram, and the reference three-dimensional volume according to the training order, comprises:

calculating the loss value using a preset loss function based on the training pseudo-sinogram, the training three-dimensional volume, the reference pseudo-sinogram, and the reference three-dimensional volume, wherein the preset loss function is a function of a weighted summation of a first loss function and a second loss function; the first loss function is configured to calculate a mean square error loss between a training pseudo-sinogram and a reference pseudo-sinogram, and the second loss function is configured to calculate a mean square error loss of a training three-dimensional volume and a reference three-dimensional volume.

7. The method according to claim 3, wherein the calculating a loss value based on the training pseudo-sinogram, the training three-dimensional volume, the reference pseudo-sinogram, and the reference three-dimensional volume according to the training order, comprises;

calculating the loss value using a preset loss function based on the training pseudo-sinogram, the training three-dimensional volume, the reference pseudo-sinogram, and the reference three-dimensional volume, wherein the preset loss function is a function of a weighted summation of a first loss function and a second loss function; the first loss function is configured to calculate a mean square error loss between a training pseudo-sinogram and a reference pseudo-sinogram, and the second loss function is configured to calculate a mean square error loss of a training three-dimensional volume and a reference three-dimensional volume.

8. The method according to claim 4, wherein the calculating a loss value based on the training pseudo-sinogram, the training three-dimensional volume, the reference pseudo-sinogram, and the reference three-dimensional volume according to the training order comprises:

calculating the loss value using a preset loss function based on the training pseudo-sinogram, the training three-dimensional volume, the reference pseudo-sinogram, and the reference three-dimensional volume, wherein the preset loss function is a function of a weighted summation of a first loss function and a second loss function: the first loss function is configured to calculate a mean square error loss between a training pseudo-sinogram and a reference pseudo-sinogram, and the second loss function is configured to calculate a mean square error loss of a training three-dimensional volume and a reference three-dimensional volume.

9. A three-dimensional computer tomography (CT) imaging device based on X-ray dual projection, comprising:

a storage unit, configured to store a preset three-dimensional volume reconstruction model; generating the preset three-dimensional volume reconstruction model comprises: obtaining a training data set; wherein the training data set is composed of digital radiography (DR) images of reference objects collected circumferentially; training to-be-trained three-dimensional volume reconstruction model using DR images with a perpendicular relationship in the training data set to obtain the preset three-dimensional volume reconstruction model;

an acquisition unit, configured to collect two DR images with a perpendicular relationship for an object to be imaged;

an obtaining unit, configured to obtain a three-dimensional volume of the object to be imaged corresponding to the two DR images with a perpendicular relationship based on the preset three-dimensional volume reconstruction model; and an imaging unit, configured to slice the three-dimensional volumes to obtain three-dimensional CT imaging of the object to be imaged, wherein, generating the three-dimensional volume reconstruction model stored in the storage unit comprises:

when obtaining the training data set, obtaining a reference three-dimensional volume and a reference pseudo-sinogram of each of the reference objects based on the training data set; wherein the reference pseudo-sinogram is obtained by stacking collected DR images of a same reference object into a three-dimensional matrix according to a collection order, summing sinograms in each layer column by column, and normalizing a sum result;

dividing the DR images of each reference object in the training data set into a plurality of DR image groups, and each of the DR image groups comprises two DR images with a perpendicular relationship;

inputting the plurality of DR image groups into the to-be-trained three-dimensional volume reconstruction model, training the to-be-trained three-dimensional volume reconstruction model, and respectively obtaining a training pseudo-sinogram and a training three-dimensional volume;

calculating a loss value based on the training pseudo-sinogram, the training three-dimensional volume, the reference pseudo-sinogram and the reference three-dimensional volume according to a training sequence;

terminating the training and obtaining the preset three-dimensional volume reconstruction model in a case that any calculated loss value is less than a target loss value, or the number of training times reaches a target number of times.

10. An electronic device, comprising a memory, a processor, and a computer program stored in the memory and executable by the processor, the processor is configured to execute the computer program to implement a three-dimensional computed tomography (CT) imaging method based on X-ray dual projection, the method comprises:

collecting two digital radiography (DR) images with a perpendicular relationship for an object to be imaged;

obtain a three-dimensional volume of the object to be imaged corresponding to the two DR images with a perpendicular relationship based on a preset three-dimensional volume reconstruction model; and slicing the three-dimensional volume to obtain three-dimensional CT imaging of the object to be imaged, wherein, generating the preset three-dimensional volume reconstruction model comprises:

obtaining a training data set; wherein the training data set is composed of DR images of reference objects collected circumferentially;

training to-be-trained three-dimensional volume reconstruction model using DR images with a perpendicular relationship in the training data set to obtain the preset three-dimensional volume reconstruction model;

wherein, when obtaining the training data set, the method further comprises:

obtaining a reference three-dimensional volume and a reference pseudo-sinogram of each of the reference objects based on the training data set; wherein the reference pseudo-sinogram is obtained by stacking collected DR images of a same reference object into a three-dimensional matrix according to a collection order, summing sinograms in each layer column by column, and normalizing a sum result;

dividing the DR images of each reference object in the training data set into a plurality of DR image groups, and each of the DR image groups comprises two DR images with a perpendicular relationship;

wherein the training to-be-trained three-dimensional volume reconstruction model using DR images with a perpendicular relationship in the training data set to obtain the preset three-dimensional volume reconstruction model comprises:

inputting the plurality of DR image groups into the to-be-trained three-dimensional volume reconstruction model, training the to-be-trained three-dimensional volume reconstruction model, and respectively obtaining a training pseudo-sinogram and a training three-dimensional volume;

calculating a loss value based on the training pseudo-sinogram, the training three-dimensional volume, the reference pseudo-sinogram and the reference three-dimensional volume according to a training order;

terminating the training and obtaining the preset three-dimensional volume reconstruction model in a case that any calculated loss value is less than a target loss value, or the number of training times reaches a target number of times.

11. The electronic device according to claim 10, wherein the to-be-trained three-dimensional volume reconstruction model comprises an enhancement network model and a reconstruction network model;

the enhancement network model is a model based on an encoder-decoder network architecture, and configured to input a DR image group with a perpendicular relationship and output a corresponding training pseudo-sinogram; and the reconstruction network model is an autoencoder network model for two-dimensional to three-dimensional volume mapping, and configured to input the training pseudo-sinogram and output a corresponding training three-dimensional volume.

12. The electronic device according to claim 11, wherein the enhancement network model to input a DR image group with a perpendicular relationship, and output a corresponding training pseudo-sinogram, comprises:

performing pattern and feature extraction on the input DR image group, and performing a cascade operation on a result of the extraction;

performing latent space feature encoding on features after the cascade operation to obtain encoded latent space features; and decoding the encoded latent space features to obtain the training pseudo-sinogram.

13. The electronic device according to claim 11, wherein the reconstruction network model to input the training pseudo-sinogram and output a corresponding training three-dimensional volume, comprises:

performing feature capture and enhancement on the input training pseudo-sinogram;

encoding a result of feature enhancement, and continuously reducing the spatial resolution on the basis of keeping the number of channels unchanged; and decoding a result of the encoding, and continuously restoring the spatial resolution to a spatial resolution of the reference three-dimensional volume to obtain the training three-dimensional volume.

14. The electronic device according to claim 10, wherein the calculating a loss value based on the training pseudo-sinogram, the training three-dimensional volume, the reference pseudo-sinogram, and the reference three-dimensional volume according to the training order, comprises:

calculating the loss value using a preset loss function based on the training pseudo-sinogram, the training three-dimensional volume, the reference pseudo-sinogram, and the reference three-dimensional volume, wherein the preset loss function is a function of a weighted summation of a first loss function and a second loss function; the first loss function is configured to calculate a mean square error loss between a training pseudo-sinogram and a reference pseudo-sinogram, and the second loss function is configured to calculate a mean square error loss of a training three-dimensional volume and a reference three-dimensional volume.

15. The electronic device according to claim 11, wherein the calculating a loss value based on the training pseudo-sinogram, the training three-dimensional volume, the reference pseudo-sinogram, and the reference three-dimensional volume according to the training order, comprises;

calculating the loss value using a preset loss function based on the training pseudo-sinogram, the training three-dimensional volume, the reference pseudo-sinogram, and the reference three-dimensional volume, wherein the preset loss function is a function of a weighted summation of a first loss function and a second loss function; the first loss function is configured to calculate a mean square error loss between a training pseudo-sinogram and a reference pseudo-sinogram, and the second loss function is configured to calculate a mean square error loss of a training three-dimensional volume and a reference three-dimensional volume.

16. The electronic device according to claim 12, wherein the calculating a loss value based on the training pseudo-sinogram, the training three-dimensional volume, the reference pseudo-sinogram, and the reference three-dimensional volume according to the training order, comprises:

calculating the loss value using a preset loss function based on the training pseudo-sinogram, the training three-dimensional volume, the reference pseudo-sinogram, and the reference three-dimensional volume, wherein the preset loss function is a function of a weighted summation of a first loss function and a second loss function; the first loss function is configured to calculate a mean square error loss between a training pseudo-sinogram and a reference pseudo-sinogram, and the second loss function is configured to calculate a mean square error loss of a training three-dimensional volume and a reference three-dimensional volume.

17. The electronic device according to claim 13, wherein the calculating a loss value based on the training pseudo-sinogram, the training three-dimensional volume, the reference pseudo-sinogram, and the reference three-dimensional volume according to the training order, comprises:

calculating the loss value using a preset loss function based on the training pseudo-sinogram, the training three-dimensional volume, the reference pseudo-sinogram, and the reference three-dimensional volume, wherein the preset loss function is a function of a weighted summation of a first loss function and a second loss function; the first loss function is configured to calculate a mean square error loss between a training pseudo-sinogram and a reference pseudo-sinogram, and the second loss function is configured to calculate a mean square error loss of a training three-dimensional volume and a reference three-dimensional volume.

* * * * *